(12) United States Patent
Birdwell et al.

(10) Patent No.: US 7,497,620 B2
(45) Date of Patent: Mar. 3, 2009

(54) METHOD AND SYSTEM FOR A MULTIPLE FOCAL SPOT X-RAY SYSTEM

(75) Inventors: Thomas William Birdwell, Middletown, OH (US); Andrew Joseph Galish, West Chester, OH (US)

(73) Assignee: General Electric Company, Schenectady, NY (US)

( * ) Notice: Subject to any disclaimer, the term of this patent is extended or adjusted under 35 U.S.C. 154(b) by 140 days.

(21) Appl. No.: 11/277,680

(22) Filed: Mar. 28, 2006

(65) Prior Publication Data

US 2007/0237303 A1 Oct. 11, 2007

(51) Int. Cl.
  *A61B 6/00* (2006.01)
(52) U.S. Cl. ..................................... 378/205
(58) Field of Classification Search .................. 378/10, 378/11, 205, 137
  See application file for complete search history.

(56) References Cited

U.S. PATENT DOCUMENTS

| | | | | |
|---|---|---|---|---|
| 4,171,476 A | * | 10/1979 | Waltham | 378/11 |
| 4,472,822 A | * | 9/1984 | Swift | 378/10 |
| 4,618,970 A | * | 10/1986 | Rand et al. | 378/10 |
| 4,718,075 A | * | 1/1988 | Horn | 378/137 |
| 5,097,492 A | | 3/1992 | Baker et al. | |
| 5,119,408 A | | 6/1992 | Little et al. | |
| 5,489,781 A | | 2/1996 | Mohr et al. | |
| 5,519,225 A | | 5/1996 | Mohr et al. | |
| 6,167,110 A | | 12/2000 | Possin et al. | |
| 6,507,635 B2 | | 1/2003 | Birdwell et al. | |
| 6,687,334 B2 | | 2/2004 | Galish et al. | |
| 6,711,235 B2 | | 3/2004 | Galish et al. | |
| 6,826,255 B2 | | 11/2004 | Birdwell et al. | |
| 6,856,667 B2 | | 2/2005 | Ellengogen | |
| 6,895,079 B2 | | 5/2005 | Birdwell et al. | |
| 7,065,176 B2 | | 6/2006 | Moermond et al. | |
| 2004/0190675 A1 | * | 9/2004 | Birdwell et al. | 378/137 |
| 2004/0202289 A1 | * | 10/2004 | Settergren et al. | 378/209 |

OTHER PUBLICATIONS

Peschmann et al., "High-speed computed tomography: systems and performance", Applied Optics, Dec. 1, 1985, vol. 24, No. 23, pp. 4052-4060.*

* cited by examiner

*Primary Examiner*—Chih-Cheng G Kao
(74) *Attorney, Agent, or Firm*—Adams Intellectual Property Law, P.A.; William Scott Andes, Esq.

(57) ABSTRACT

A radiographic inspection system includes an electron gun, a fixed anode of a dense material, and apparatus for steering an electron beam generated by the electron gun to multiple focal spots on the anode. A detector includes a plurality of individual detector elements. Operation of the system includes is carried out by directing the electron beam at a first time interval to a first focal spot on the anode, generating a first X-ray beam aligned with a first detector element. During a second time interval, the electron beam is directed to a second focal spot on the anode, spaced-away from the first focal spot, generating a second X-ray beam aligned with a second detector element. This cycle is repeated with additional focal spots in a one-dimensional or two-dimensional pattern. The detector element output is read in coordination with the position of the electron beam.

15 Claims, 5 Drawing Sheets

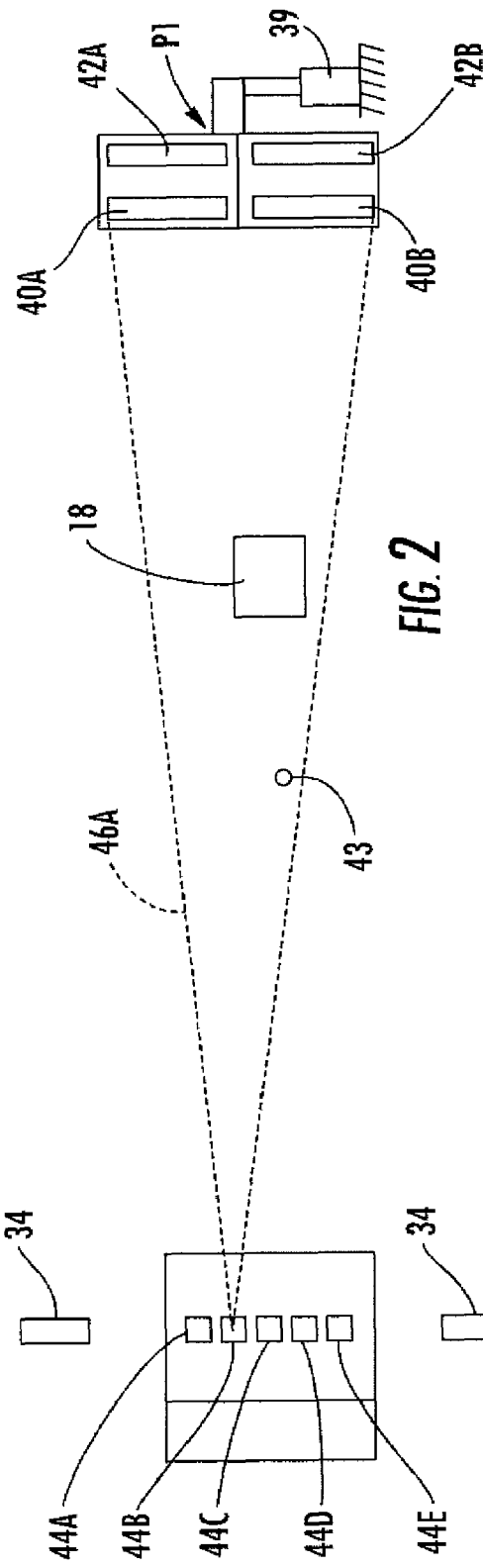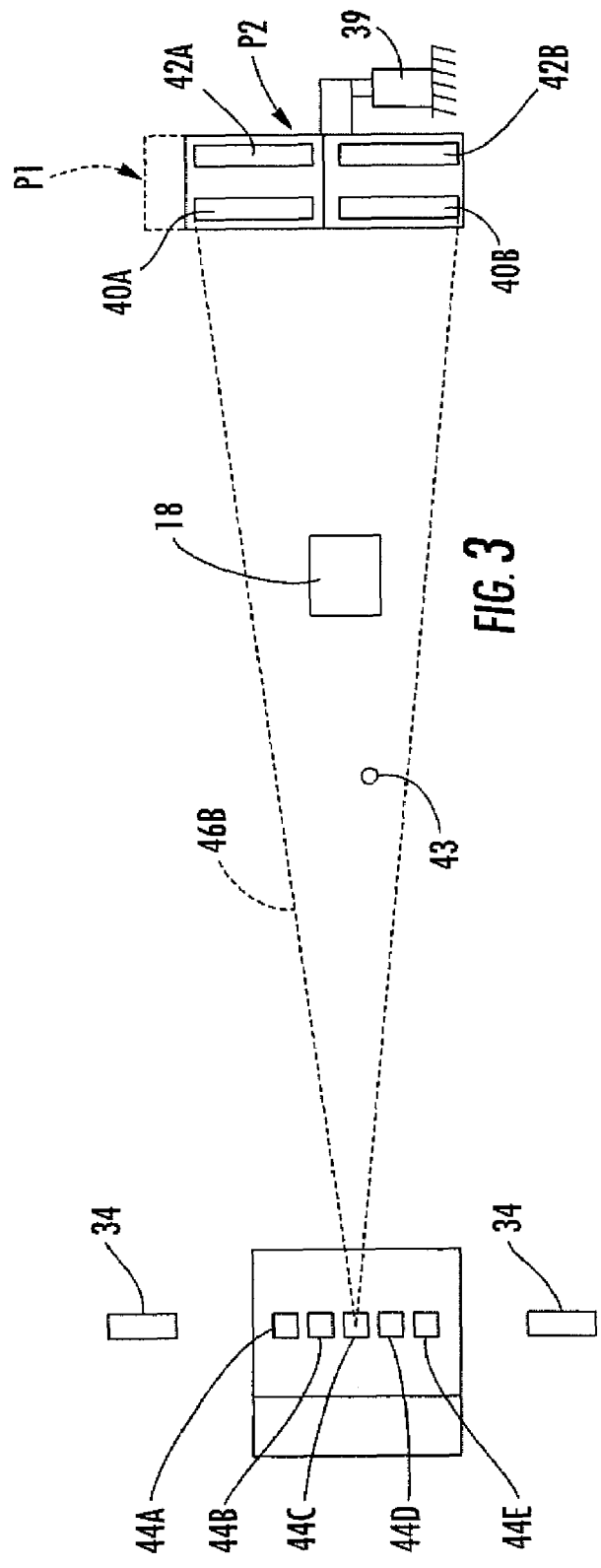

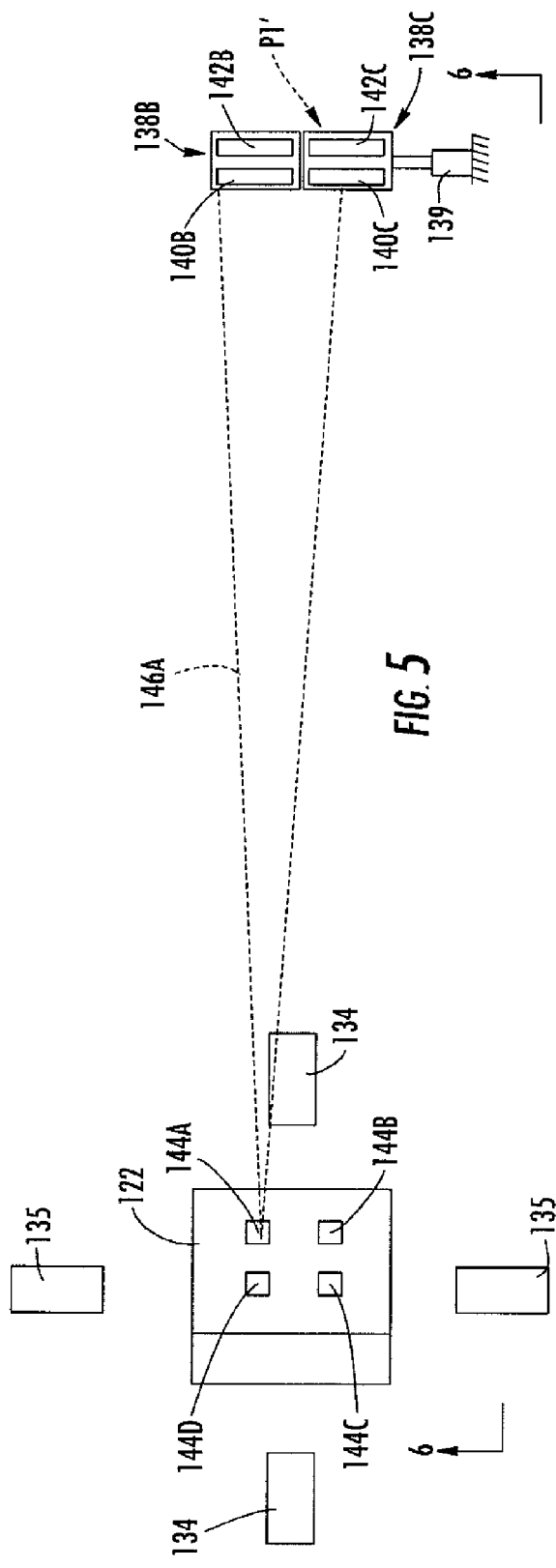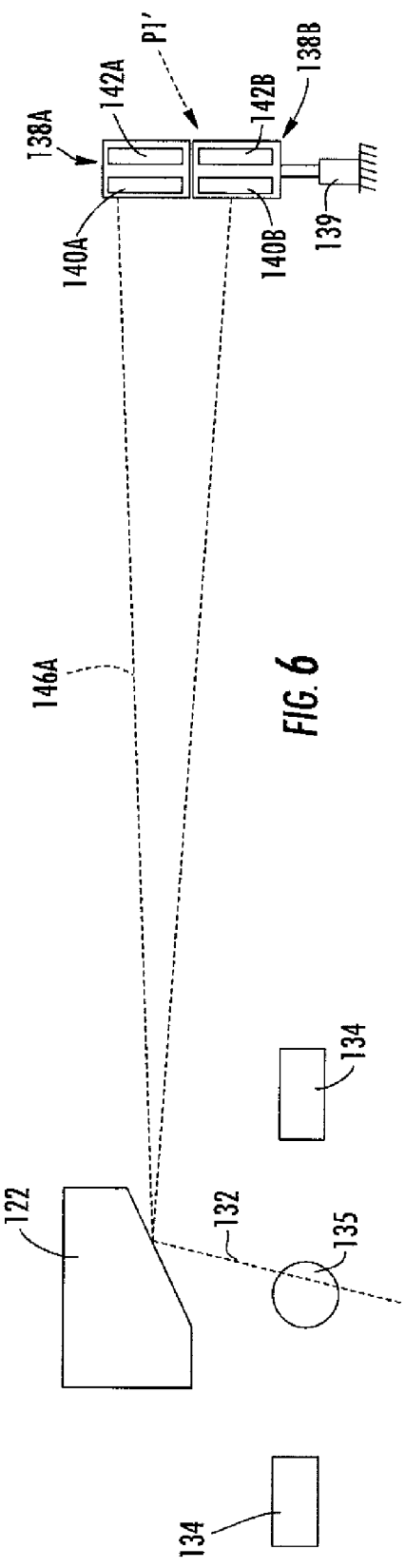

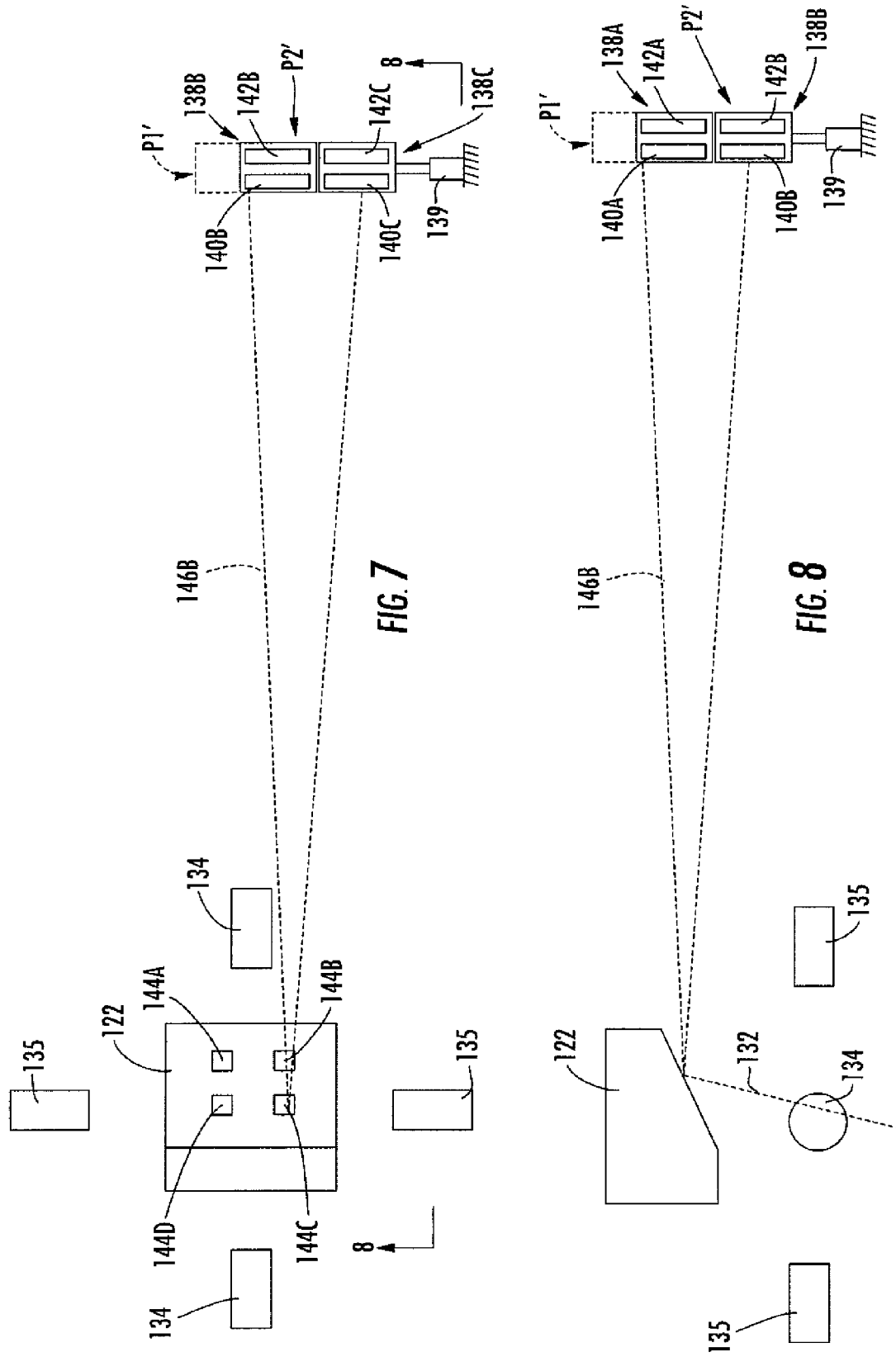

METHOD AND SYSTEM FOR A MULTIPLE FOCAL SPOT X-RAY SYSTEM

BACKGROUND OF THE INVENTION

This invention relates generally to radiographic inspection systems, and more particularly to a method of operating a radiographic source with a fixed anode.

X-ray tubes produce X-rays by accelerating electrons into a tungsten or other dense target. During this process, as much as 99 percent of the tube's electrical energy becomes thermal energy. Ideally an x-ray tube would produce a large x-ray output flux from a very small x-ray focal spot to produce high quality images in a short period of time. Unfortunately, these two requirements compete. Inspection time and spot cooling capability are directly related to the X-ray output, which is directly related to the focal spot size. However, focal spot size is inversely related to image resolution. Therefore, trade-offs must be made between tube life, inspection speed, and image quality.

Prior art fixed anode X-ray tubes provide moderate focal spot sizes with relatively low output flux. They offer a low cost, high reliability source of x-rays for continuous use in radiographic inspections. Rotating anode tubes move a metallic target in front of a fixed electron beam, increasing the effective target cooling area and permitting improved tube output while maintaining focal spot size. This requires a mechanism to rotate the anode while maintaining anode cooling and tube vacuum. These requirements generally increase tube cost and reduce tube life when compared to fixed anode tubes.

Accordingly, there is a need for a method of operating a fixed anode X-ray inspection system to increase cooling capability while maintaining a small focal spot size.

BRIEF SUMMARY OF THE INVENTION

The above-mentioned need is met by the present invention, which according to one aspect provides a method for operating a radiographic inspection system, including the steps of: providing an X-ray source including an electron gun, a fixed anode of a dense material, and steering means for directing an electron beam generated by the electron gun; providing a detector to receive radiation emitted from the radiation source, the detector operable to produce an output in response to radiation flux thereupon; providing detector coordination means for effectively translating the output; during a first time interval, directing the electron beam to a first focal spot on the anode so as to generate a first X-ray beam which strikes the detector; during a second time interval, directing the electron beam to a second focal spot on the anode, spaced-away from the first focal spot, so as to generate a second X-ray beam which strikes the detector; and translating the output of detector in coordination with the position of the electron beam.

According to another aspect of the invention, a radiographic inspection system includes an X-ray source including an electron gun, a fixed anode of a dense material, and means for steering an electron beam generated by the electron gun; a detector disposed to receive radiation emitted from the radiation source, the detector operable to produce an output in response to radiation flux thereupon; means for sequentially directing the electron beam to selected ones of a plurality of focal spots on the anode, so as to sequentially generate corresponding X-ray beams; means for reading an output of each of the detector elements in coordination with the position of the electron beam; and detector coordination means for effectively translating the output in coordination with the position of the electron beam.

BRIEF DESCRIPTION OF THE DRAWINGS

The invention may be best understood by reference to the following description taken in conjunction with the accompanying drawing figures in which:

FIG. 2 is a view taken along lines 2-2 of FIG. 1 while an X-ray beam is directed at a first detector element;

FIG. 3 is a view taken along lines 2-2 of FIG. 1 while an X-ray beam is directed at a second detector element;

FIG. 5 is a view taken along lines 5-5 of FIG. 4 while an X-ray beam is directed at a first detector element;

FIG. 6 is a view taken along lines 6-6 of FIG. 5;

FIG. 7 is a view taken along lines 7-7 of FIG. 4 while an X-ray beam is directed at a second detector element; and FIG. 8 is a view taken along lines 8-8 of FIG. 7.

DETAILED DESCRIPTION OF THE INVENTION

Figure 1:
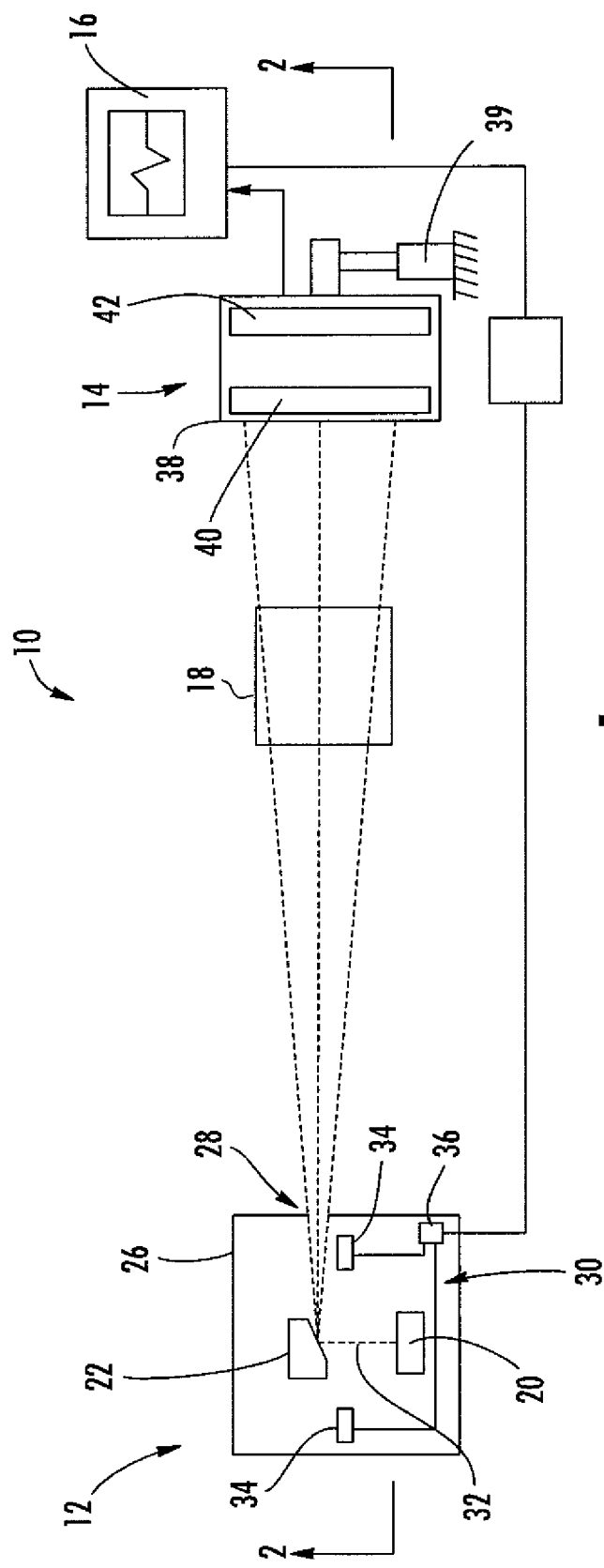
FIG. 1 is a schematic side view of a radiographic inspection system constructed according to the present invention.

Referring to the drawings wherein identical reference numerals denote the same elements throughout the various views, FIG. 1 illustrates an exemplary X-ray inspection system 10 constructed in accordance with the present invention. The inspection system 10 comprises an X-ray source 12, a detector 14, and a detector reading means 16. A target 18 to be inspected is disposed between the source 12 and the detector 14. The X-ray source 12 includes an electron gun 20 of a known type and a fixed anode 22 of a dense material (such as tungsten) which emits X-rays when bombarded by electrons.

The X-ray source 12 includes a housing 26 which encloses the electron gun 20 and the anode 22. The housing 26 has an aperture 28 formed therein, which may be a simple opening or may be covered with a material transparent to X-rays. Beam steering means 30 are mounted in the housing 26 so as to be able to control the direction of an electron beam 32 generated by the electron gun 20. For example, a plurality of electromagnetic deflection coils 34 of a known type, such as those used in electron-beam welding apparatus, may be mounted in the housing 26. In the illustrated example, first and second deflection coils 34 are mounted opposite each other along a line perpendicular to the electron beam 32, so as to be able to generate an electromagnetic field which deflects the electron beam 32 in a vertical plane. Additional deflection coils (not shown) may be used if it is desired to deflect the beam in other directions, or to focus the electron beam 32. The deflection coils 34 are connected to a source of current flow such as a coil power supply 36 of a known type. The electron beam 32 may also be steered by an electrostatic field created between a pair of deflection plates (not shown) connected to a power supply in a known manner.

In the illustrated example, the detector 14 is of a known type such as a linear detector, however the present invention may be applied to any electronic detector with the capability of synchronizing the detector's sampling period in unison with the source's beam steering sampling period. The detector 14 includes a plurality of adjacent detector elements 38 arranged side-by-side or in a two-dimensional array (only one element 38 is visible in FIG. 1). Depending upon the specific application, the detector 14 may be constructed in an arc shape (not shown) for use with a fan-shaped X-ray beam. Each detector element 38 is shown schematically as comprising a scintillator component 40 which produces optical photons when struck by ionizing radiation and a photoelectric component 42 such as a photodiode which produces an electrical signal when struck by optical photons. This electrical signal is the detector's output. Some types of detectors convert X-ray flux to electric charge without a scintillator.

For purposes of illustration, an exemplary detector reading means 16 is depicted as a simple oscilloscope which displays a graphical representation of the signal output of the detector 14. It is to be understood that the detector reading means 16 may be any known device or combination of devices for displaying, measuring, storing, analyzing, or processing the signal from the detector 14, and that the term "reading" is intended to include any or all of the above-listed processes. In a typical computed tomography (CT) system or digital radiography (DR) system, the detector reading means 16 would comprise a sampling device (not shown) of a known type for receiving and storing the signals from the detector 14, for example an array of charge integrating amplifiers or an array of current to voltage amplifiers followed by an integrating stage. The sampling device is connected to separate means for processing and displaying an image constructed from the detector output, such as a computer and monitor.

FIG. 2 illustrates the X-ray inspection system 10 during a first time interval in an inspection process. The electron gun 20 emits an electron beam 32 (FIG. 1). The deflection coils 34 are used to focus the electron beam 32 and align it so that it travels in a first direction and strikes the anode 22 at a first focal spot 44B. In response, the anode 22 emits a first X-ray beam 46A. The first X-ray beam 46A passes through the target 18, where it is attenuated to varying degrees depending on the density and structure of the target 18. The first X-ray beam 46A then strikes the scintillator components 40A and 40B of the detector element 38, which emit optical photons that subsequently strike the photoelectric components 42A and 42B and cause a charge to build up therein.

FIG. 3 illustrates the X-ray inspection system 10 at a second time interval. The electron gun 20 continues to emit an electron beam 32 as described above. The deflection coils 34 are used to focus the electron beam 32 and align it so that it travels in a second direction and strikes the anode 22 at a second focal spot 44C. In response, the anode 22 emits a second X-ray beam 46B. The second X-ray beam 46B is aligned with the detector 38. This alignment may be carried out using various methods. In the illustrated example, the detector 38 is physically translated, for example using an actuator 39 of a known type, from a first position "P1", shown in FIG. 2, to a second position "P2", shown in FIG. 3, with the amount of translation being proportional to the distance between the focal spots 44B and 44C. The translation could also be effectuated by leaving the detector 38 stationary and using known digital processing techniques within the detector reading means 16 to "virtually" translate the output image, relative to the received X-ray flux pattern, by the desired amount.

The translation process, whether physical or digital, may be enhanced by placing one or more artifacts of a known shape and size (shown schematically at 43) within the beam path. The artifact 43 provides a fixed point of reference in the flux pattern and output image which can be used to determine the proper direction and magnitude of a required translation.

The second X-ray beam 46B passes through the target 18, where it is attenuated to varying degrees depending on the density and structure of the target 18. The second X-ray beam 46B then strikes the scintillator components 40A and 40B of the second detector 38, which emits optical photons that subsequently strike the photoelectric components 42 and cause a charge to build up therein.

This beam-shifting process continues for as many focal spot—detector position pairs as desired. For example five separate focal spots 44A-44E are depicted in FIGS. 2 and 3. In operation, the electron beam 32 would be continuously sequenced through each of these focal spots 44A-44E, and would be shifted away from each particular focal spot long enough for it to cool adequately before striking that spot again. The electron beam 32 may be shifted to adjacent focal spots 44A-44E sequentially, or it may be shifted in a random order. The detector 38 undergoes a corresponding physical or virtual shift each time the electron beam 32 is shifted. Each discrete focal spot 44A-44E is located sufficiently distant from the others to allow increased total combined area for spot cooling, while maintaining each focal spot 44A-44E at a desired small spot size. This increase in effective cooling area will permit higher tube X-ray output relative to prior art fixed anode tubes.

FIGS. 4-8 illustrate an alternative X-ray inspection system 110 which is substantially similar to the inspection system 10 described above and includes an X-ray source 112, a detector 114, a detector reading means 116, and a controller 141. The X-ray source 112 includes an electron gun 120 of a known type and a fixed anode 122.

The X-ray source 112 includes a housing 126 which encloses the electron gun 120 and the anode 122. Beam steering means 130 are mounted in the housing 126 so as to be able to control the direction of an electron beam 132 generated by the electron gun 120. In the illustrated example, a plurality of electromagnetic deflection coils of a known type, such as those used in electron-beam welding apparatus, are mounted in the housing 126. In the illustrated example, first and second deflection coils 134 are mounted opposite each other along a line perpendicular to the electron beam 132, so as to be able to generate an electromagnetic field which deflects the electron beam 132 in a vertical plane. Additional deflection coils 135 are used to deflect the beam in a perpendicular plane. The deflection coils 134 and 135 are connected to a source of current flow such as a coil power supply 136 of a known type.

The detector 114 is a known type of area detector having a plurality of adjacent detector elements 138A-138C (138D not shown) arranged in a two-dimensional array Depending upon the specific application, the detector 14 may be constructed in an arc shape (not shown) for use with a fan-shaped X-ray beam. Each detector element 138A-138C is shown schematically as comprising a scintillator component 140A-140D (140D not shown) which produces optical photons when struck by ionizing radiation and a photoelectric component 142A-142C (142D not shown) such as a photodiode which produces an electrical signal when struck by optical photons.

Figure 4:
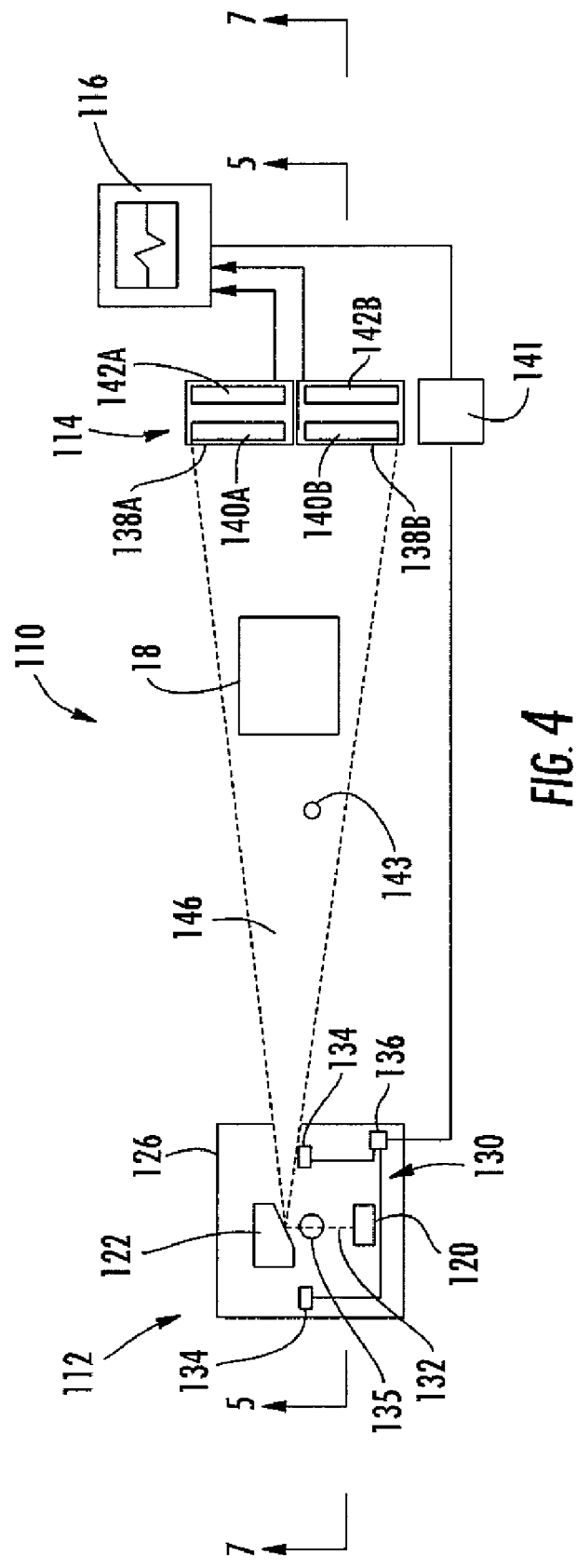
FIG. 4 is a schematic side view of an alternative radiographic inspection system constructed according to the present invention.

FIGS. 5 and 6 illustrate the X-ray inspection system 110 during a first time interval and a second time interval in an inspection process, respectively. During the inspection process, the electron gun 120 emits an electron beam 132 (FIG. 4). The beam steering means 130 are used to focus the electron beam 132 and align it so that it travels in a desired direction and strikes the anode 122 at a desired focal spot 144. In response, the anode 122 emits an X-ray beam 146.

During the inspection process, the electron beam 132 is shifted and the detector 138 is read substantially as described above. However, the electron beam 132 is shifted in two dimensions instead of one. For example, in FIGS. 5 and 6, the electron beam 132 is aimed in a first direction and strikes the anode 122 at a first focal spot 144A. In response, the anode 122 emits a first X-ray beam 146A. In FIGS. 7 and 8, the electron beam 132 is aimed in a second direction and strikes the anode 122 at a second focal spot 144C. This second focal spot 144C is offset from the first focal spot 144A in both "X" and "Y" directions. In response, the anode 122 emits a second X-ray beam 146B. The detector 138 is physically or virtually translated in both "X" and "Y" directions in coordination with the movement of the X-ray beam 146, substantially as described above for the detector 38, for example using actuators 139. The detector 138 is moved from a first position "P1" (FIGS. 5 and 6) to a second position "P2" (FIGS. 7 and 8). One or more artifacts 143, similar to the artifacts 43 described above, may be provided for alignment purposes.

This beam-shifting process continues for as many focal spot—detector position pairs as desired. For example four separate focal spots 144A-144D are depicted in FIGS. 5 and 6. In operation, the electron beam 132 would be continuously sequenced through each of these focal spots 144A-144D, and would be shifted away from each particular focal spot long enough for it to cool adequately before striking that spot again. The electron beam 132 may be shifted to adjacent focal spots sequentially, or it may be shifted in a random order. The detector 138 undergoes a corresponding physical or virtual shift each time the electron beam 132 is shifted. Each discrete focal spot 144A-144D is located sufficiently distant from the others to allow increased total combined area for spot cooling, while maintaining each focal spot 144A-144D at a desired small spot size. This increase in effective cooling area will permit higher tube X-ray output relative to prior art fixed anode tubes.

The foregoing has described a radiographic inspection system and a method for its operation. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation, the invention being defined by the claims.

What is claimed is:

1. A method for operating a radiographic inspection system, comprising the steps of:
    providing an X-ray source including an electron gun, a fixed anode of a dense material, and deflection coils for directing an electron beam generated by said electron gun in only a first direction, wherein said deflection coils are positioned within a housing and proximate the electron beam;
    providing a detector to receive radiation emitted from said X-ray source, said detector operable to produce an electrical output in response to radiation flux thereupon;
    providing detector coordination means for linearly translating said detector;
    during a first time interval, directing said electron beam to a first focal spot on said anode so as to generate a first X-ray beam which strikes said detector;
    during a second time interval, using said deflection coils to direct said electron beam to a second focal spot on said anode, spaced-away from said first focal spot, so as to generate a second X-ray beam which strikes said detector, wherein said second focal spot is positioned at a distance from the first focal spot to allow cooling of the first focal spot; and
    translating said electrical output produced by said detector in coordination with the position of said electron beam, wherein said detector coordination means linearly translate said detector a distance proportional to the distance between said first focal spot and said second focal spot, and wherein said first X-ray beam and said second X-ray beam travel undeflected towards the detector.

2. The method of claim 1 wherein said detector coordination means comprise at least one actuator for physically moving said detector in coordination with the movement of said electron beam.

3. The method of claim 1 wherein said detector coordination means comprise digital image translation means.

4. The method of claim 1 further comprising:
    during a subsequent time interval, directing said electron beam using said deflection coils to a subsequent focal spot on said anode, spaced-away from said first and second focal spots, so as to generate a subsequent X-ray beam aligned with a subsequent one of a plurality of detector elements of said detector.

5. The method of claim 1 wherein said anode includes a plurality of said focal spots, and wherein said electron beam is sequentially directed to said focal spots using said deflection coils such that each focal spot is allowed to cool before said electron beam is redirected thereto.

6. The method of claim 1 wherein said detector is a linear detector comprising an array of side-by-side detector elements.

7. The method of claim 1 wherein said detector is an area detector comprising a two-dimensional array of detector elements.

8. A radiographic inspection system including;
    an X-ray source including an electron gun, a fixed anode of a dense material, and means for steering an electron beam generated by said electron gun in a first direction;
    a detector disposed to receive radiation emitted from said X-ray source, said detector operable to produce an electronic output in response to radiation flux thereupon;
    a deflection coil positioned within a housing and proximate the electron beam for sequentially directing said electron beam to a selected one of a plurality of focal spots on said anode, so as to sequentially generate corresponding X-ray beams, wherein each focal spot of the plurality of focal spots is positioned at a distance from each other focal spot of the plurality of focal spots to allow cooling of each focal spot of the plurality of focal spots;
    means for reading the electronic output of each of a plurality of detector elements of said detector in coordination with the position of said electron beam; and
    detector coordination means for linearly translating said detector in coordination with the position of said electron beam, wherein said detector coordination means linearly translate the detector a distance proportional to the distance between each focal spot, and wherein said corresponding X-ray beams travel undeflected towards the detector.

9. The system of claim 8 wherein said means for reading said detector elements includes a sampling device operably connected to a programmable controller.

10. The system of claim 9 wherein said controller is operable to cause said sampling device to read the output of each of said detector elements while that detector element is being struck with X-rays.

11. The system of claim 9 wherein said controller is operable to cause said sampling device to read the output of each of said detector elements after that detector element has been struck with X-rays.

12. The system of claim 8 further comprising:
    means for directing said electron beam using said deflection coil to a subsequent focal spot on said anode, spaced-away from first and second focal spots, so as to generate a subsequent X-ray beam aligned with said detector.

13. The system of claim 8 wherein said anode includes a plurality of said focal spots, and wherein said electron beam is sequentially directed using said deflection coil to said focal spots such that each focal spot is allowed to cool before said electron beam is redirected thereto.

14. The system of claim 8 wherein said detector is a linear detector comprising an array of side-by-side detector elements.

15. The system of claim 8 wherein:
said detector is an area detector comprising a two-dimensional array of detector elements, and said deflection coils comprise:
a first pair of spaced-apart deflection coils operable to direct said electron beam along a first axis; and
a second pair of spaced-apart deflection coils operable to direct said electron beam along a second axis perpendicular to said first axis.

* * * * *